United States Patent [19]

Davey et al.

[11] Patent Number: 4,544,654

[45] Date of Patent: Oct. 1, 1985

[54] SUBSTITUTED SULFONAMIDOBENZAMIDES, ANTIARRHYTHMIC AGENTS AND COMPOSITIONS THEREOF

[75] Inventors: David D. Davey, Succasunna, N.J.; William C. Lumma, Jr., Pennsburg, Pa.; Ronald A. Wohl, Morris Plains, N.J.

[73] Assignee: Schering A.G., Berlin, Fed. Rep. of Germany

[21] Appl. No.: 591,649

[22] Filed: Mar. 20, 1984

[51] Int. Cl.$^4$ .................. A61K 31/18; A61K 31/535; C07C 143/75; C07C 143/80
[52] U.S. Cl. ................ 514/210; 260/239 A; 260/239 B; 514/212; 514/218; 514/222; 514/229; 514/255; 514/329; 514/330; 514/423; 514/426; 514/603; 514/604; 514/605; 544/58.1; 544/58.2; 544/58.5; 544/58.6; 544/160; 544/391; 546/244; 548/539; 564/80; 564/83; 564/85; 564/86; 564/89; 564/91; 564/99
[58] Field of Search ............ 564/80, 83, 85, 86, 564/89, 91, 99; 260/239 A, 239 B; 544/58.1, 58.2, 58.5, 58.6, 160, 391; 546/244; 548/539; 424/246, 248.5, 250, 267, 274, 244

[56] References Cited

U.S. PATENT DOCUMENTS

| | | | |
|---|---|---|---|
| 3,995,044 | 11/1976 | Kabbe et al. | 424/263 |
| 4,034,106 | 7/1977 | Smith | 424/304 |
| 4,049,821 | 9/1977 | Funderburk, Jr. | 424/274 |
| 4,301,159 | 11/1981 | Ogata et al. | 424/230 |
| 4,328,344 | 5/1982 | Masaru et al. | 546/208 |
| 4,350,635 | 9/1982 | Ogata et al. | 424/274 X |

*Primary Examiner*—Richard L. Raymond
*Attorney, Agent, or Firm*—Elizabeth A. Bellamy; John L. White; I. William Millen

[57] ABSTRACT

Novel substituted sulfonamidobenzamides are described as useful antiarrhythmic agents. Their use in the treatment of cardiac arrhythmias, especially re-entrant arrhythmias, via the prolongation of the action potential of cardiac tissue is provided. Pharmaceutical formulations containing such compounds are also disclosed.

28 Claims, No Drawings

SUBSTITUTED SULFONAMIDOBENZAMIDES, ANTIARRHYTHMIC AGENTS AND COMPOSITIONS THEREOF

PRIOR ART

The compounds described herein provide antiarrhythmic efficacy by prolongation of ventricular refractoriness with no effect on conduction in the cardiac tissue. These compounds, as opposed to the known drugs procainamide and acecainide, do not cause conduction disturbances, are not arrhythmogenic (in doses to 30 times the effective dose) and do not depress cardiac function.

FIELD OF THE INVENTION

This invention relates to novel substituted sulfonamidobenzamides and their use as antiarrhythmic agents. Specifically, this invention relates to novel substituted 4-sulfonamidobenzamides and their pharmaceutically acceptable salts, to pharmaceutical compositions containing them as active ingredients and to the method of using them in the treatment of arrhythmias, more especially, in the treatment of re-entrant arrhythmias.

GENERAL DESCRIPTION OF THE INVENTION

Composition-of-Matter Aspect

In its composition-of-matter aspect this invention relates to novel substituted sulfonamidobenzamides and their pharmaceutically acceptable salts. Particularly, this invention relates to the novel compounds defined by the following Formula I:

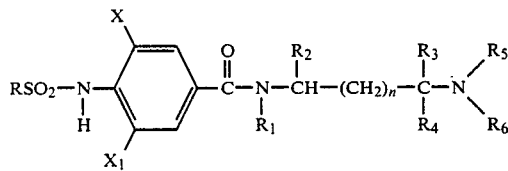

wherein R is loweralkyl, cycloalkyl, cycloalkyl(lower)alkyl, benzyl, benzyl substituted by halogen, loweralkyl, loweralkoxy, or loweralkyl substituted by hydroxy, loweralkoxy, carbamoyl, N-loweralkylcarbamoyl, N,N-diloweralkylcarbamoyl and sulfamoyl.

X and $X_1$ are the same or independently hydrogen or halogen.

$R_1$ is hydrogen, lower alkyl, unsaturated loweralkyl, loweralkoxyloweralkyl, or collectively with $R_2$ is an alkylene chain forming an azetidine, pyrrolidine, piperidine or a hexahydroazepine ring, or collectively with $R_3$ is a bond or an alkylene chain forming an azetidine, pyrrolidine, piperidine or a hexahydroazepine ring. Similarly, $R_1$ collectively with $R_5$ may produce a piperazine or a hexahydro-1,4-diazepine ring system.

$R_2$ is hydrogen, loweralkyl or collectively with $R_3$ is a bond or an alkylene chain to form a saturated carbocyclic ring of from 4 to 8 ring carbon atoms.

$R_3$ and $R_4$ are the same or independently hydrogen, loweralkyl, or collectively are an alkylene chain forming a saturated carbocyclic ring of from 4 to 6 ring carbon atoms.

$R_5$ and $R_6$ are the same or independently unsaturated loweralkyl, $C_1$-$C_{12}$ straight or branched chain alkyl, $C_3$-$C_6$ cycloalkyl, cycloalkyl(lower)alkyl, or when taken together form a saturated heterocyclic ring of from 4 to 8 members which may be substituted by one or more methyl groups or optionally include a —O—, S $O_p$ linkage, wherein p is an integer of 0, 1 or 2. $R_6$ can also be loweralkyl substituted by phenyl which may be substituted by up to 3 substituents selected from hydoxy or methoxy groups.

In this invention n is an integer of 0, 1 or 2.

With the proviso that:

(a) when any of $R_1$, $R_5$ and $R_6$ is unsaturated loweralkyl, the unsaturation cannot be alpha to the nitrogen atom.

Also contemplated as part of this invention are the pharmaceutically acceptable salts of the compounds of Formula I. Useful acids for this purpose include inorganic acids such as hydrochloric, hydrobromic, sulfuric or phosphoric and organic acids such as acetic, propionic, benzoic, naphthoic, oxalic, succinic, maleic, malic, adipic, lactic, tartaric, citric, salicylic, methanesulfonic and p-toluenesulfonic.

It is to be understood that the definition of the compounds of Formula I encompasses all possible stereoisomers and mixtures thereof, which possess the activity discussed below. In particular, it encompasses racemic modifications and any optical isomers which possess the indicated activity.

In the above Formula I, halogen represents fluorine, chlorine, bromine and iodine, loweralkyl shall refer to a straight or branched chain of from 1 to 4 carbon atoms, unsaturated loweralkyl shall refer to a straight or branched chain of from 3 to 4 carbon atoms having present a double or triple bond. Cycloalkyl shall be taken to mean a saturated carbocyclic of from 3 to 6 carbon atoms and cycloalkyl(lower)alkyl shall contain 4 to 10 carbon members.

Preferred classes of compounds embodied by this invention are those of the above general Formula I having one or more of the following characteristics:

(a) R is lower alkyl,
(b) X and $X_1$ are hydrogen,
(c) $R_1$, $R_2$, $R_3$ and $R_4$ are hydrogen,
(d) $R_5$ and $R_6$ are $C_1$-$C_{12}$ straight or branched chain alkyl,
(e) $R_1$ and $R_5$ form a piperazine ring, and $R_2$, $R_3$ and $R_4$ are hydrogen.

The more preferred compounds of this invention are those containing the above a, b, and e characteristics.

The most preferred compounds of this invention are those containing the above a, b, c and d characteristics.

The compounds which follow are some of those which serve to exemplify various aspects of the invention described herein.

(1) N-[2-(Diethylamino)ethyl]-4-[(methylsulfonyl)amino]benzamide.

(2) N-[3-(Diethylamino)propyl]-4-[(methylsulfonyl)amino]benzamide.

(3) 4-[(Butylsulfonyl)amino]-N-[2-(diethylamino)ethyl]benzamide.

(4) N-[2-(Diethylamino)ethyl]-4-[(ethylsulfonyl)amino]benzamide.

(5) 4-[(Methylsulfonyl)amino]-N-[2-(4-morpholinyl)ethyl]benzamide.

(6) 4-Methyl-1-[4-[(methylsulfonyl)amino]benzoyl]piperazine.

(7) 4-[(Methylsulfonyl)amino]-N-[2-(1-piperidinyl)ethyl]benzamide.

(8) 4-[(Methylsulfonyl)amino]-N-[2-(1-pyrrolidinyl)ethyl]benzamide.

(9) N-[4-(Diethylamino)butyl]-4-[(methylsulfonyl)amino]benzamide.
(10) N-[2-(Diethylamino)ethyl]-N-methyl-4-[(methylsulfonyl)amino]benzamide.
(11) N-[4-[[2-(Diethylamino)ethyl]aminocarbonyl]phenyl]benzenemethanesulfonamide.
(12) 4-[(Methylsulfonyl)amino]-N-[2-(2,2,6,6-tetramethylpiperidino)ethyl]benzamide.
(13) N-[2-(Dimethylamino)ethyl]-4-[(methylsulfonyl)amino]benzamide.
(14) 4-[(Methylsulfonyl)amino]-N-[2-(thiomorpholin-4-yl)ethyl]benzamide.
(15) N-[2-(Dipropylamino)ethyl]-4-[(methylsulfonyl)amino]benzamide.
(16) N-[2-(Diisopropylamino)ethyl]-4-[methylsulfonyl)amino]benzamide.
(17) N-[2-(Ethylamino)ethyl]-4-[(methylsulfonyl)amino]benzamide.
(18) 4-[(Methylsulfonyl)amino]-N-[2-(1-oxo-thiomorpholin-4-yl)ethyl]benzamide.
(19) N-[(1-(Diethylamino)cyclopent-1-yl)methyl]-4-[(methylsulfonyl)amino]benzamide.
(20) N-[2-(Ethyl(heptyl)amino)ethyl]-4-[(methylsulfonyl)amino]benzamide.
(21) N-[2-(Ethyl(pentyl)amino)ethyl]-4-[(methylsulfonyl)amino]benzamide.
(22) N-[2-(Cyclohexylmethyl(methyl)amino)ethyl]-4-[(methylsulfonyl)amino]benzamide.
(23) N-[2-(Cyclohexyl(methyl)amino)ethyl]-4-[(methylsulfonyl)amino]benzamide.
(24) N-[2-(Dicyclopropylamino)ethyl]-4-[(methylsulfonyl)amino]benzamide.
(25) N-[2-(Diallylamino)ethyl]-4-[(methylsulfonyl)amino]benzamide.
(26) N-Allyl-N-[2-(diethylamino)ethyl]-4-[(methylsulfonyl)amino]benzamide.
(27) N-[2-(Dibutylamino)ethyl]-4-[(methylsulfonyl)amino]benzamide.
(28) N-[3-(2-Methyl-1-piperidinyl)propyl]-4-[(methylsulfonyl)amino]benzamide.
(29) N-[3-(3-methyl-1-piperidinyl)propyl]-4-[(methylsulfonyl)amino]benzamide.
(30) N-[2-((1,1-Dimethylethyl)amino)ethyl]-4-[(methylsulfonyl)amino]benzamide.
(31) 2-[(Diethylamino)methyl]-1-[4-[(methylsulfonyl)amino]benzoyl]pyrrolidine.
(32) N[2-[2-(3,4-Dimethoxyphenyl)ethyl(ethyl)amino]ethyl]4-[(methylsulfonyl)amino]benzamide.
(33) 4-[2-(3,4-Dimethoxyphenyl)ethyl]-1-[4-[(methylsulfonyl)amino]benzoyl]piperazine.

Process Aspect

In general, the compounds of this invention may be prepared by various processes and reactants known in the art. In order to produce the compounds of Formula I and intermediates thereto the following schemes were most usually employed.

Scheme A

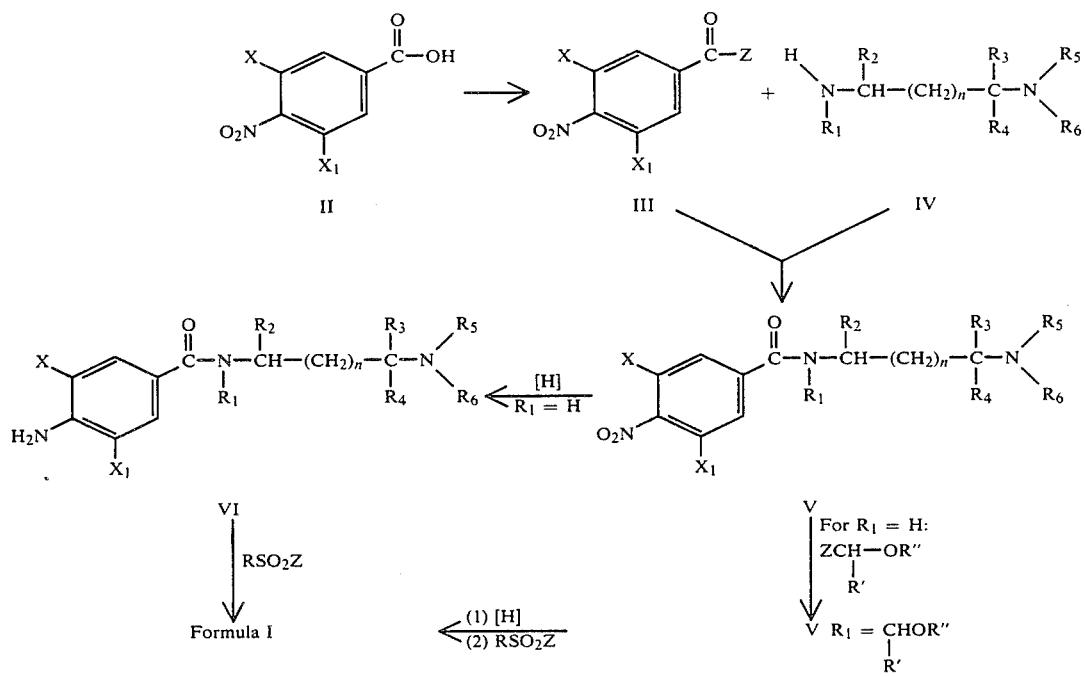

Z = halogen, loweralkoxy,

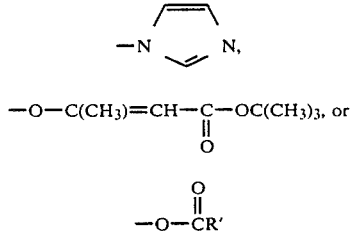

R′ = loweralkyl;
R″ = loweralkyl or loweralkanoyl of 2–5 carbon atoms (straight or branched chain).

In the approach as illustrated in the foregoing Scheme A, a substituted nitrobenzoic acid (II) is activated as the acyl halide or ester or acylimidazole or alternatively using an alkyl chloroformate is activated as the anhydride. The preparation of the active intermediates (III) is conducted in an anhydrous aprotic solvent such as chloroform, hexane, acetonitrile or N,N-dimethylformamide at temperatures from about 31 50° C. to +50° C., preferably at about 0° C. The condensation of compounds (III) with known in the art α,ω-diamines (IV) is accomplished in aprotic solvents at temperatures from about −50° C. to +50° C. under anhydrous conditions to produce the nitro-benzamide intermediates (V). These intermediates (V) may be reduced via catalytic hydrogenation (or other chemical means), thence the sulfonamide is produced to provide the compounds of this invention (I).

Alternatively, the intermediates of (V) may be converted at $R_1$ when $R_1$ is H to compounds wherein $R_1$ is

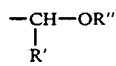

(VII), thence they are hydrogenated and reacted to produce the sulfonamides of other Formula I compounds.

In yet another pathway to compounds of Formula I, p-nitrobenzoic acid is reduced to p-aminobenzoic acid, thence treated to produce the sulfonamide, which is then activated to compounds III as in Scheme A. These compounds are condensed with the α,ω-diamines to produce compounds of Formula I.

Still another route to preparing the compound of this invention is reacting the p-aminobenzamide intermediate VI of Scheme A with trialkylsilylhalide or bis[trialkylsilyl]amine to form the N-trialkylsilyl intermediate. These latter compounds are reacted with $RSO_2$ halide to give the compounds of Formula I.

To produce intermediates such as 1-diethylamino-1-(2-amino)alkylcyclopentanes the following scheme is provided.

tion is possible for a compound, separation is accomplished by the usual methods such as chromatography or cystallization. When crystallization is used, it is frequently done after conversion to a salt with an acid that is not optically active. Alternatively, it is possible to obtain optically active products by the use of optically active starting materials.

Method-Of-Use And Pharmaceutical Composition Aspect

The substituted sulfonamidobenzamides of this invention and their pharmaceutically acceptable salts are antiarrhythmic agents. There compounds are useful in the treatment of cardiac arrhythmias, especially those of the re-entrant type and particularly those associated with the disease state known as chronic ventricular tachycardia.

The action of the compounds of this invention is attributed to their ability to prolong the action potential of the cardiac tissue. Therefore, they are Class III antiarrhythmic agents within the Vaughan-Williams classification of antiarrhythmic agents. Such activity has been analyzed in several procedures, for instance, utilizing standard electrophysiological techniques to measure resting potential, action potential amplitude, duration, rate of rise and refractory periods of normal canine Purkinje fibres; and also utilizing re-entrant arrhythmias induced by programmed electrical stimulation in the conscious dog.

In the United States all of the drugs currently available for the treatment of chronic ventricular tachycardia (e.g. disopyramide, procainamide and quinidine) act by slowing conduction of the electrical impulses within the heart. Thus, these drugs are grouped as Class I antiarrhythmic agents within the Vaughan-Williams classification. As a direct consequence, of their Class I modus operandi these compounds also cause conduction disturbances (they are arrhythmogenic) and depress cardiac function. For example, procainamide, when studied in vitro, prolongs action potential duration but also slows action potential upstroke (Goodman & Gilman, 6th Ed., 1980, pg. 768). This finding correlates with conduction slowing (i.e. conduction disturb- Scheme B

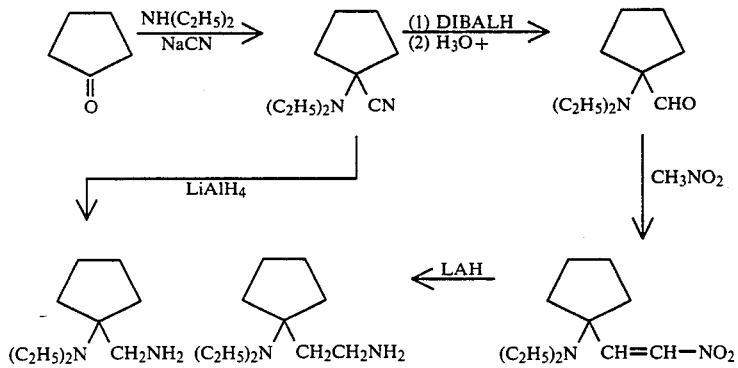

There may be one or more asymmetric centres present in the compounds of this invention so that at least one or more pairs of optical isomers is possible. The individual optical isomers can be obtained from a racemic modification by standard procedures such as forming a salt with an optically active acid followed by crystallization. Where more than one racemic modificaances) in the in situ heart. Further, procainamide, when studied in vivo, causes cardiovascular depression at doses approximating the therapeutic dose (20–40 mg/kg) and blocks ganglionic and vagal transmission (Lertora, Stec, Kushner & Eudidkis, Proc. Soc. Exp.

Biol. Med., 164:128–136, 1976 & Pearle, Sousa & Gillis, J. Cardiovasc. Pharmacol., 5:450–453, 1983).

In contradistinction, the compounds of this invention, exemplified by N-[2-(diethylamino)ethyl]-4-[(methylsulfonyl)amino]benzamide hydrochloride, prolong action potential duration without slowing the action potential upstroke (it may be increased). Therefore, there are no conduction disturbances in the heart. No local anesthetic action (a causal factor of slow conduction) can be elicited with doses up to 50–100 times the concentration which prolongs action potential duration by 20%. In vivo, there is no evidence for cardiovascular depression at doses 10 to 30 times the therapeutic dose (1–3 mg/kg) nor is there any evidence for effects on ganglionic or vagal transmission in doses up to 10 mg/kg (i.e., 3–10 times the effective dose). Thus the compounds of this invention in contrast to procainamide demonstrate greater potency with respect to prolongation of action potential duration, have no effect on conduction of the cardiac potential, and have no effect, whether direct or indirect, on cardiovascular function at doses 10 to 30 times the therapeutic dose.

The N-acetylated metabolite of procainamide known as acecainide has also been reported to have antiarrhythmic activity. Acecainide has little effect on conduction of the cardiac action potential, but does prolong refractoriness which characteristic categorizes it as a Class III antiarrhythmic agent.

Compounds of the present invention exemplified by N-[2-(diethylamino)ethyl]-4-[(methylsulfonyl)amino]benzamide hydrochloride differ significantly from acecainide in a number of respects. They are 10 to several hundred times as potent as acecainide in prolonging action potential duration in canine cardiac Purkinje fibers. When tested in a model of re-entrant ventricular tachycardia in anesthetized dogs they are 10 times more potent than acecainide. As stated above, the compounds of this invention cause no hemodynamic depression whereas acecainide, like procainamide causes such depression at doses approximating the therapeutic dose.

The major limiting side effect in the use of procainamide in man is drug induced lupus erythematosis. Acecainide has also been shown to cause lupus. Although the incidence is significantly lower than for procainamide the problem remains since it has been shown that acecainide is deacetylated in man. The compounds of this invention are not metabolized to procainamide; therefore, it is unlikely that drug-induced lupus will be a limiting side effect with their use.

In an in vitro bacterial test for mutagenicity (the Ames Test) procainamide demonstrated significant mutagenic potential at levels as low as 0.2 mg/plate. In the same test system acecainide was found to be one-half as active as a mutagen. On the other hand, when N-[2-(diethylamino)ethyl]-4-[(methylsulfonyl)amino]benzamide hydrochloride was submitted to the Ames test with essentially the same procedures no significant mutagenic potential was demonstrated at levels up to 5 mg/plate.

Thus there is provided by this invention a method for treating arrhythmia which comprises administering to a subject suffering from an arrhythmia and in need of treatment or to a subject suspected of developing an arrhythmia an effective amount for treating such arrhythmia of a compound of this invention. The compounds are preferably utilized for the control of re-entrant arrhythmias in humans and for the treatment of chronic ventricular tachycardia.

In general, the compounds of this invention may be administered orally or parenterally. The dosage administered will be dependent on the subject being treated, the route of administration and the type and severity of the arrhythmia being prevented or reduced.

The compound to be administered can be formulated by admixing with any of a number of suitable pharmaceutical diluents and carriers such as lactose, sucrose, starch powder, cellulose, calcium sulfate, sodium benzoate and the like. Such formulations can be compressed into tablets or can be encapsulated into gelatin capsules for convenient oral administration. Such a capsule may contain one of the compounds of this invention for example, N-[2-(diethylamino)-4-[(methylsulfonyl)amino]benzamide hydrochloride in the amount of about 1 to about 500 mg. Such formulation can be administered orally at the rate of about 1 to 4 capsules per day or more often as needed, depending upon the particular condition and subject being treated.

For parenteral administration a compound of this invention can be formulated as an intramuscular or intravenous medicament but is not limited thereto. In the case of treatment of a patient suffering from a severe cardiac arrhythmia, it may be desirable to administer a compound of the invention by intravenous slow bolus in order to effect a rapid conversion to a normal sinus rhythm. The normalized condition can then be maintained by oral administration.

The compounds of this invention can be formulated for parenteral administration with any of a number of pharmaceutically acceptable carriers and diluents to constitute an injectable liquid solution. Commonly used diluents and carriers include water or a saline solution, buffered aqueous solutions as well as dispersing and surface active agents if necessary. A typical formulation suited to intravenous or intramuscular administration may contain one of the compounds of this invention such as N-[2-(diethylamino)ethyl]-4-[(methylsulfonyl)amino]benzamide hydrochloride in the amount of about 50 to 150 mg and a solubilizing agent and sufficient sterile water to bring the volume to about 5 ml–100 ml. Such formulation can be infused at a constant rate or injected one to four times per day or more often depending upon the particular condition of the subject being treated.

It is further contemplated that the compounds of this invention may be formulated into sublingual lozenges or impregnated into fabric appliques for a type of transdermal application.

The pharmaceutical preparations of the compounds of this invention may optionally, additionally contain one or more other pharmaceutically active substances. As for instance combining the compounds of this invention with β-adrenergic blocking agents for the treatment of mammalian subjects who have suffered myocardial infarction.

The invention described hereinabove is illustrated below in the Preparations and Examples, which, however, are not to be construed as limiting the scope of this invention.

PREPARATIONS

Preparation 1

4-[(Methylsulfonyl)amino]benzoic acid

To 215.2 g (2.72 mole) of pyridine in 1250 ml of dichloromethane is added 238 g (1.44 mole) of ethyl 4-aminobenzoate. After cooling to 0° C., a solution of 177.6 g (1.55 mole) of methanesulfonyl chloride in 250 ml of dichloromethane is added with stirring. Upon completion of the addition, the ice bath is removed and the reaction is stirred for one hour at room temperature.

The reaction mixture is extracted with 3×500 ml of 4N sodium hydroxide and the aqueous extract is first washed with 3×500 ml of dichloromethane and then with 3×250 ml of ether. The aqueous extract is refluxed for two hours and allowed to cool overnight. The reaction is acidified with concentrated hydrochloric acid until a white precipitate forms. Collection by filtration followed by drying provides 310 g of the title compound.

NMR (DMSO-$d_6$): $\delta$=3.2(s,3), 7.25–7.55(m,2) and 7.85–8.20 (m,2)ppm.

Preparation 2

4-[(Methylsulfonyl)amino]benzoic acid sodium salt

To 500 ml of water is added 63.4 g (1.59 mole) of sodium hydroxide and the mixture is stirred until all the solid has dissolved. To this is slowly added 310 g (1.44 mole) of 4-[(methylsulfonyl)amino]benzoic acid. The reaction is stirred for 15 minutes at ambient temperature after all the solid has dissolved. After removal of the water in vacuo, the residue is triturated with isopropyl alcohol, evaporated, triturated with acetone and concentrated in vacuo. The solid is dried under vacuum for 72 hours to provide 333.7 g of the title compound.

NMR (DMSO-$d_6$): $\delta$=3.0(s,3), 5.3–5.8(br s,2), 7.0–7.3 (m,2) and 7.8–8.1(m,2)ppm.

Preparation 3

4-[(Methylsulfonyl)amino]benzoyl chloride

To 600 ml of thionyl chloride at 0° C. is added 150 g (0.63 mole) of 4-[(methylsulfonyl)amino]benzoic acid sodium salt under a nitrogen atmosphere and the reaction is refluxed for 40 hours. The excess thionyl chloride is removed in vacuo and the crude product triturated with toluene and evaporated. After dissolving the solid in tetrahydrofuran, charcoal is added, and the mixture filtered through Celite. Concentration in vacuo provides a solid which is then slurried with cold ether and collected by filtration. Drying for 18 hours in vacuo provides 133 g of the title compound.

NMR (DMSO-$d_6$): $\delta$=3.2(s,3), 7.3–7.6(m,2) and 7.9–8.2 (m,2)ppm.

Preparation 4

2-[Ethyl(heptyl)amino]acetonitrile

Combine 7.95 g (0.055 moles) ethyl(heptyl)amine, 3.5 ml (0.055 moles) chloroacetonitrile, 5.8 g (0.055 moles) sodium carbonate and 25 ml toluene in a sealed pressure tube. Heat to 125° C. for 18 hrs. Follow the progress of the reaction by thin layer chromatography on silica gel ($CH_3CN$+MeOH+$NH_4OH$, 85+10+5). At the completion of the reaction, filter the reaction mixture and evaporate the solvents to provide the title compound.

NMR (CDCl$_3$): $\delta$=0.4–1.75(m,21), 2.3–2.8(t,4) and 3.6(s,2)ppm.

Preparation 5

N-Ethyl-N-heptyl-1,2-ethanediamine

Suspend 1.2 g (0.032 moles) lithium aluminum hydride in 20 ml THF. Chill the suspension to −10° C. under a stream of $N_2$. Slowly add 7.90 g (0.043 moles) 2-[ethyl(heptyl)amino]acetonitrile to the suspension. Stir for 2 hrs at ambient temperature. Quench the reaction mixture with $Na_2SO_4 \cdot 10H_2O$ and $H_2O$. Filter the quenched reaction mixture and evaporate the solvents to provide the title compound. (B.P.: 42°–45° C./0.015 mmHg).

NMR (CDCl$_3$): 300 MHz $\delta$=0.80–0.94(t,3), 0.94–1.06(t,3), 1.16–1.54(m,10), 1.82(s,2), 2.34–2.60 (m,6) and 2.66–2.80(t,2)ppm.

EXAMPLES

Example I

N-[2-(Diethylamino)ethyl]-4-[(methylsulfonyl)amino]-benzamide hydrochloride

To 100 ml of anhydrous tetrahydrofuran is added 10 g (0.0429 mole) of 4-[(methylsulfonyl)amino]benzoyl chloride and the reaction is cooled in an ice bath. A solution of 5.0 g (0.043 mole) of N,N-diethylethylenediamine in 25 ml of tetrahydrofuran is added over 15 minutes. The solvent is decanted and the precipitate is triturated with 100 ml of ether and crystallized from 100 ml of acetone with three drops of methanol. After cooling, the resultant solid is washed with acetone and dried in vacuo to provide the title compound.

NMR (D$_2$O): $\delta$=1.35(t,6), 3.18(s,3), 3.36(q,4), 3.46 (t,2), 3.82(t,2), 7.36(d,2) and 7.84 (d,2)ppm.

Example II

General Procedure

Dissolve 10 g (0.043 mole) of 4-[(methylsulfonyl)amino]benzoyl chloride in 350 ml tetrahydrofuran. Cool to 0° C., and add a solution of 0.041 mole of the appropriate diamino compound in 50 ml of tetrahydrofuran dropwise over 15 minutes. Stir at 0° C. for 30 minutes. Stir at room temperature for 30 minutes. Filter the precipitate, and wash with acetone. Recrystallize from ethanol to provide the title compound.

Substitute the following diamino compounds in the above general procedure:
(a) 3-(Diethylamino)propylamine
(b) N-(2-Aminoethyl)morpholine
(c) N-Methylpiperazine
(d) N-(2-Aminoethyl)piperidine
(e) N-(2-Aminoethyl)pyrrolidine
(f) 4-(Diethylamino)butanamine
(g) N,N-Diethyl-N'-methylethylenediamine To provide the following compounds:

(1)

N-[3-(Diethylamino)propyl]-4-[(methylsulfonyl)amino]benzamide

Convert to the free base. Purify by recrystallization from ethyl acetate.

NMR (DMSO-$d_6$): $\delta$=0.8–1.0(t,6), 1.5–1.7(m,2), 2.3–2.5(m,6), 3.0(s,3), 3.2–3.3(m,2), 7.2(d,2), 7.8(d,2) and 8.4(br s,1)ppm.

(2)

4-[(Methylsulfonyl)amino]-N-[(2-(4-morpholinyl)ethyl]benzamide hydrochloride

NMR (D$_2$O): $\delta$=3.2(s,3), 3.4–3.6(m,6), 3.8–3.9(t,2), 3.9–4.1(br s,4), 7.4(d,2) and 7.8–7.9(d,2)ppm.

(3)

4-Methyl-1-[4-[(methylsulfonyl)amino]benzoyl]piperazine

The hydrochloride is converted to the hydrobromide. Purify by recrystallization from ethanol.

NMR (D$_2$O): δ=2.9(s,3), 3.2(s,3), 3.2–4.0(m,8) and 7.3–7.6(2d,4)ppm.

(4)
4-[(Methylsulfonyl)amino]-N-[2-(1-piperidinyl)ethyl]-benzamide hydrochloride NMR (D$_2$O): δ=1.4–2.1(m,6), 2.9–3.2(m,5), 3.3–3.4 (t,2), 3.5–3.9(m,4), 7.4(m,2) and 7.8–7.91(m,2)ppm.

(5)
4-[(Methylsulfonyl)amino]-N-[2-(1-pyrrolidinyl)ethyl]-benzamide hydrochloride NMR (D$_2$O): δ=2.0–2.3(m,4), 3.1–3.9(m,11), 7.4 (d,2) and 7.9(d,2)ppm.

(6)
N-[4-(Diethylamino)butyl]-4-[(methylsulfonyl)amino]-benzamide

NMR(DMSO-d$_6$): (60 MHz) δ=1.21(t,6), 1.37–1.93(m,4), 2.70–3.65 (m,8), 3.05(s,3), 7.30(d,2), 7.93 (d,2), 8.62(t,1) and 10.42(br s,2)ppm.

(7)
N-[2-(Diethylamino)ethyl]-N-methyl-4-[(methylsulfonyl)amino]benzamide

NMR (DMSO-d$_6$): δ=0.91(t,6), 2.41(m,6), 2.53(m,2), 2.61(s,3), 2.95(s,3), 6.82(d,2) and 7.08(d,2)ppm.

Example III

4-[(Methylsulfonyl)amino]-N-[2-(1-oxo-thiomorpholin-4-yl)ethyl]benzamide

To 50 ml of methanol add 1.0 g (2.93 mmole) of 4-[(methylsulfonyl)amino]-N-[2-(thiomorpholin-4-yl)ethyl]benzamide. Add dropwise 3.08 ml (3.08 mmole) of 1.0N hydrochloric acid. Cool the solution to 0° C. Slowly add 0.70 ml (6.16 mmole) of 30% w/v hydrogen peroxide. Stir the reaction at ambient temperature. Monitor the progress of the reaction by thin layer chromatography on silica gel (methanol:1M NaCl; 95:5). Upon the completion of the reaction, add 25 ml of 10% sodium sulfite to the stirring solution. Filter the resulting solid. Evaporate the filtrate in vacuo to yield a solid. Stir this solid in H$_2$O overnight, then filter the solid and recrystallize it from methanol to yield the title compound.

NMR(DMSO-d$_6$): (60 MHz) δ=2.40–2.95(m,10), 3.03(s,3), 3.13–3.60(m,2), 7.08–7.33(d,2), 7.60–7.88(d,2), 8.20(t,1) and 9.60–10.20(br s,1)ppm.

Example IV

N-[4-[[2-(Diethylamino)ethyl]aminocarbonyl]phenyl]-benzenemethanesulfonamide hydrochloride To a solution of 7.1 g (0.026 moles) of procainamide hydrochloride in 100 ml acetone and 5 ml triethylamino at −50° C., is added slowly 5.0 g (0.026 moles) of α-toluenesulfonyl chloride. Stir at −50° C. for 1 hour, then warm to room temperature and stir for 16 hours. Remove the solvent in vacuo. Slurry the residue in 200 ml ether, and wash 2×100 ml portions of methylene chloride. The combined methylene chloride extracted are vacuum stripped to dryness. The residue is dissolved in 100 ml ethanol and brought to pH 3 with concentrated hydrochloric acid. The solvent is removed in vacuo, and the residue triturated with methylene-chloride to provide the title compound.

NMR(DMSO-d$_6$): δ=1.1–1.5(t,6), 3.0–3.9(m,11), 4.6(s,2), 7.2–7.6(m,7), 7.9–8.1(d,2) and 8.9–9.1(m,1)ppm.

Example V

4-[(Butylsulfonyl)amino]-N-[2-(diethylamino)ethyl]-benzamide hydrobromide

To 100 ml of methylene chloride add 6.52 g (36.2 mmole) of 4-amino-N-[2-(diethylamino)ethyl]benzamide and cool to −78° C. under nitrogen atmosphere. To this solution slowly add 5.61 g (36.2 mmole) of n-butanesulfonyl chloride. When the addition is complete, allow the reaction mixture to warm to room temperature and monitor by thin layer chromatography on silica gel (acetonitrile:ammonium hydroxide, 9:1). Upon completion of the reaction remove the solvent in vacuo. To the resulting oil add 50 ml H$_2$O followed by 50% sodium hydroxide until pH=14. Extract the aqueous layer with 3×50 ml diethyl ether and 2×25 ml of methylene chloride. To the aqueous layer add concentrated HCl to bring the pH to 8.5. Extract the aqueous solution with 3×75 ml of methylene chloride. Combine the extracts and dry over sodium sulfate. Filter the drying agent and remove the solvent in vacuo. Dissolve the resulting oil in acetonitrile. Bubble HBr gas through the solution until pH=1. Remove the solvent in vacuo. Triterate the resulting oil in diethyl ether and ethyl acetate to yield a precipitate. Isolate by filtration and recrystallize from MeOH/ethyl acetate to afford the title compound.

NMR (DMSO-d$_6$): δ=0.82(t,3), 1.22(t,6), 1.34(m,2), 1.63 (m,2), 3.23(m,8), 3.57(m,2), 7.26 (d,2), 8.67(t,1), 9.22(br s,1) and 10.19(s,1)ppm.

Example VI

N-[2-(Diethylamino)ethyl]-4-[(ethylsulfonyl)amino]-benzamide hydrochloride

Dissolve 4.97 g (0.22 moles) 4-[(ethylsulfonyl)amino]-benzoyl chloride in 25 ml THF. Stir under N$_2$ at −10° C. To the solution add 3.0 ml (0.22 mole) N,N-diethylethylenediamine dropwise. Follow the progress of the reaction by thin layer chromatography on silica gel (acetonitrile:methanol:ammonium hydroxide, 85:10:5). When the reaction is complete, remove the solvents in vacuo. Dissolve the gummy residue in refluxing ethanol and chill to produce white crystals. Filter the precipitate to obtain the title compound.

NMR (DMSO-d$_6$): δ=0.95–1.55(m,9), 2.80–4.00(m,10), 7.15–7.55(d,2), 7.80–8.20(d,2), 8.75–9.25 (t,1) and 9.75–11.25(bs,1)ppm.

Example VII

N-[(Dipropylamino)ethyl]-4-[(methylsulfonyl)amino]-benzamide hydrobromide

To 150 ml of methylene chloride under nitrogen atmosphere add 6.0 g (41.6 mmole) of N,N-dipropyl-1,2-ethanediamine and 4.42 g (43.7 mmole) of triethylamine. Cool the mixture to 0° C. Slowly add 11.44 g (48.9 mmole) of 4-[(methylsulfonyl)amino]benzoyl chloride keeping the reaction temperature below 5° C. When the addition is complete, allow the reaction mixture to stir at ambient temperature. Monitor the progress of the reaction by thin layer chromatography on silica gel (acetonitrile:ammonium hydroxide, 9:1). Upon completion of the reaction, remove the solvent in vacuo. To the resulting solid add 100 ml of water. To the solution add 50% sodium hydroxide until pH 14 is reached. Wash the aqueous with 3×50 ml of diethyl ether. Add concentrated hydrogen chloride until pH=8.5. Extract the aqueous layer with 3×100 ml of methylene chloride. Combine the extracts and dry over sodium sulfate. Remove drying agent by filtration and remove solvent in vacuo. Dissolve resulting oil in methanol and bubble HBr gas through the solution until pH=1. Add decolorizing charcoal to the solution. Remove the charcoal by filtration and remove the solvent in vacuo. Triterate the solid in ethyl acetate. Isolate the solid by filtration and recrystallize solid from acetonitrile to afford the title compound.

NMR(DMSO-d$_6$): (300 MHz) $\delta$=0.93(t,6), 1.59–1.79(m,4), 3.09(s,3), 3.12 (br s,4), 3.20(br s,2), 3.64(q,2), 7.31 (d,2), 7.92(d,2), 8.78(t,1), 9.41(br s,1) and 10.19(s,1)ppm.

Example VIII

N-[2-(diisopropylamino)ethyl]-4-[(methylsulfonyl)amino]benzamide monohydrobromide React 4-[(methylsulfonyl)amino]benzoyl chloride and 2-[bis(1-methylethyl)amino]ethanamine in a manner similar to Example VII to produce the title compound.

NMR(DMSO-d$_6$): (300 MHz) $\delta$=1.31(d,12), 3.09(s,3), 3.20(br s,2), 3.57 (q,2), 7.28(d,2), 7.85(d,2), 8.74(br s,2) and 10.20(s,1)ppm.

Example IX

4-[(Methylsulfonyl)amino]-N-[2-(thiomorpholin-4-yl)ethyl]benzamide

To 150 ml of methylene chloride under nitrogen atmosphere add 3.1 g (14.3 mmole) of 4-thiomorpholinethanamine and 4.42 g (43.6 mmole) of triethylamine. Stir the mixture at ambient temperature for 1 hour, then cool the mixture to −10° C. To the cooled mixture add slowly 3.67 g (15.1 mmole) of 4-[(methylsulfonyl)amino]benzoyl chloride, keeping the temperature below 5° C. When the addition is complete, allow the reaction mixture to stir at ambient temperature. Monitor the progress of the reaction by thin layer chromatography on silica gel (acetonitrile:ammonium hydroxide, 9:1). Upon completion of the reaction, remove the solvent in vacuo. To the resulting solid add 50 ml of water. To the mixture add 50% sodium hydroxide until pH of 14 is reached. Wash the aqueous layer with 3×50 ml of diethyl ether. Add concentrated hydrochloric acid until a white precipitate forms (pH=8.5). Filter the solid and recrystallize from methanol/ethanol to yield the title compound.

NMR(DMSO/d$_6$): $\delta$=2.51(m,2), 2.60(q,4), 2.68(q,4), 3.05(s,3), 3.30(br s,2), 7.23(d,2), 7.79(d,2), 8.28 (t,1) and 10.5(br s,1)ppm.

Example X

N-[2-(Dimethylamino)ethyl]-4-[(methylsulfonyl)amino]benzamide

In a three-neck flask equipped with mechanical stirrer, cooled in ice bath under nitrogen atmosphere, place a solution of 4.67 g (0.02 mole) of 4-[(methylsulfonyl)amino]benzoyl chloride in 30 ml of anhydrous THF. Add dropwise a solution of 1.77 g (0.02 mole) of N,N-dimethylethylenediamine in 10 ml of anhydrous THF; white solid precipitate forms immediately. Stir the mixture at ice temperature for one-half hour and at room temperature for one-half hour. Collect the solid by filtration, wash with dichloromethane, and recrystallize from methanol ether mixture to provide the title compound.

NMR(DMSO-d$_6$): (300 MHz) $\delta$=2.81(s,6), 3.07(s,3), 3.25(t,2), 3.64 (quar,2), 7.28(d,2), 7.93(d,2), 8,85(t,1) and 10.15–10.44(m,2)ppm.

Example XI

4-[(Methylsulfonyl)amino]-N-[2-(2,2,6,6-tetramethylpiperidino)ethyl]benzamide hydrochloride To 2.72 g (11.1 mmole) of 4-[(methylsulfonyl)amino]benzoyl chloride in 50 ml of tetrahydrofuran cooled to 0° C. under an N$_2$ atmosphere add dropwise 2.04 g (11.1 mmole) of N-(2-aminoethyl)-2,2,6,6-tetramethylpiperidine. After the addition is complete, allow the reaction to stir at ambient temperature overnight. Monitor the progress of the reaction by thin layer chromatography on silica gel (acetonitrile: ammonium hydroxide; 9:1). When the reaction is complete, remove the solvent in vacuo. Dissolve the resulting oil in 50 ml of water. Add 50% sodium hydroxide until pH=14. Wash aqueous with 3×50 ml of diethyl ether. To aqueous layer add concentrated hydrochloric acid until pH=9. Extract with 3×50 ml of methylene chloride. Combine extracts and dry over sodium sulfate. Remove solvent in vacuo. Dissolve resulting oil in methanol and bubble hydrogen chloride gas through the solution until pH 1 is reached. Remove the solvent in vacuo. Recrystallize the solid in methanol/ethyl acetate to provide the title compound.

NMR (DMSO-d$_6$): $\delta$=1.30(s,3), 1.48(s,6), 1.48–1.70(m,2), 1.70–1.90(m,2), 1.94–2.12(t,2), 3.16–3.24 (br s,2), 3.33(s,3), 3.54–3.66(br d,2), 7.27(d,2), 7.88(d,2), 8.90–9.00(m,2) and 10.18(s,1)ppm.

Example XII

N-[2-(Ethylamino)ethyl]-4-[(methylsulfonyl)amino]-benzamide hydrochloride

To a solution of 4.45 g (50.5 mmoles) of N-ethylethylenediamine in 50 ml of tetrahydrofuran cooled in an ice/ethanol bath under a nitrogen atmosphere add dropwise a solution of 11.8 g (50.5 mmoles) of 4-[(methylsulfonyl)amino]benzoyl chloride in 100 ml of tetrahydrofuran. When the addition is complete, allow the mixture to warm to room temperature and stir overnight. Filter the resulting solid and wash the solid with tetrahydrofuran then with diethyl ether. Triturate the solid in acetone, then recrystallize from 90% aqueous methanol to obtain the title compound.

NMR(DMSO-d$_6$): $\delta$=1.25(t,3), 2.75–3.35(m,4), 3.10(s,3), 7.33 (d,2), 8.03(d,2), 8.90(t,1) and 9.50 (br, s,2)ppm.

Example XIII

N-[2-[Ethyl(heptyl)amino)ethyl]-4-[(methylsulfonyl)amino]benzamide hydrogen phosphate salt Dissolve 5.66 g (0.024 moles) 4-[(methylsulfonyl)amino]benzoyl chloride in 40 ml THF. Chill the solution on an ice/MeOH bath under a stream of N$_2$. Add dropwise 4.5 g (0.024 moles) N-ethyl-N-heptyl-1,2-ethanediamine to the room temperature for about 24 hours. Follow the progress of the reaction by thin layer chromatography on silica gel (Acetonitrile: MeOH: Ammonia, 85:10:5). At the completion of the reaction, remove the solvents in vacuo. Dissolve the resulting oil in 10% K$_2$CO$_3$ solution and extract with 5×100 ml Et$_2$O. Dry the organics over Na$_2$SO$_4$. Evaporate the solvents to provide an oil. Crude wt: 3.38 g. Dissolve the oil in 25 ml EtOH and acidify with 1.02 g 85% H$_3$PO$_4$. Treat the solution with activated charcoal, filter and evaporate the solvents to provide the title compound. Recrystallize the product from EtOH-/Et2O.

NMR (DMSO-d6): 300 MHz δ=0.74–0.92(t,3), 1.00–1.14(t,3), 1.14–1.34(m,8), 1.40–1.60(m,2), 2.60–2.96(m,6), 3.04(s,3), 3.36–3.56 (m,2), 6.20–8.50(br s,4), 7.20–7.32 (d,2), 7.80–8.00(d,2) and 8.80(bs,1)ppm.

Contemplated as equivalents to the compounds of this invention are those of the following Formulae VIII and IX.

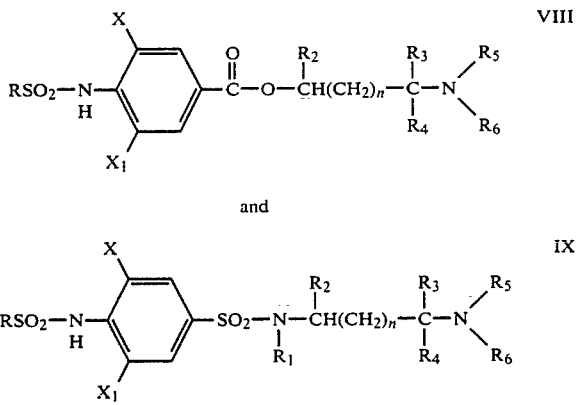

and wherein R, $R_1$, $R_2$, $R_3$, $R_4$, $R_5$, $R_6$, X, $X_1$, n, p and the pharmaceutically acceptable salts take the same meaning as in Formula I.

Formulae VIII and IX are exemplified by 4-[(methylsulfonyl)amino]benzoic acid 2-(diethylamino)ethyl ester and N-[2-(diethylamino)ethyl]-4-[(methylsulfonyl)amino]benzenesulfonamide, respectively, which compounds are also to be construed as Class III antiarrhythmic agents.

We claim:

1. A compound according to the formula:

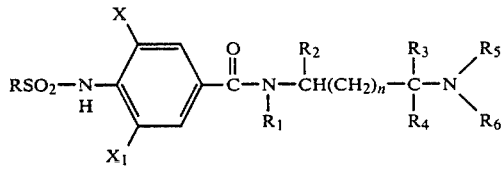

wherein
R = lower alkyl, cycloalkyl, cycloalkyl(lower)alkyl, benzyl, or benzyl substituted by halogen, loweralkyl, loweralkoxy, or lower alkyl substituted by hydroxy, lower alkoxy, carbamoyl, N-loweralkylcarbamoyl, N,N-diloweralkylcarbamoyl and sulfamoyl;

X,$X_1$ = hydrogen and halogen;

$R_1$ = hydrogen, loweralkyl, unsaturated loweralkyl, loweralkoxyloweralkyl, or collectively with $R_2$ is an alkylene chain forming an azetidine, pyrrolidine, piperidine, or hexahydroazepine ring, or collectively with $R_3$ is a bond or an alkylene chain forming an azetidine, pyrrolidine, piperidine or a hexahydroazepine ring, or collectively with $R_5$ may produce a piperazine or a hexahydro-1,4-diazepine ring system;

$R_2$ = hydrogen, loweralkyl or collectively with $R_3$ is a bond or an alkylene chain to form a saturated carbocyclic ring of from 4 to 8 ring carbon atoms.

$R_3$,$R_4$ = hydrogen, loweralkyl or collectively is an alkylene chain forming a saturated carbocyclic ring of from 4 to 6 ring carbon atoms;

$R_5$,$R_6$ = unsaturated loweralkyl, $C_1$–$C_{12}$ straight or branched chain alkyl, $C_3$–$C_6$ cycloalkyl, cycloalkyl(lower)alkyl, or when taken together form a saturated heterocyclic ring of from 4 to 8 ring members which may be substituted by one or more methyl groups or optionally contains a —O—, or

linkage wherein p is the integer 0, 1 or 2;

$R_6$ = loweralkyl substituted by phenyl which may be substituted by up to 3 substituents selected from hydroxy or methoxy groups;

n = 0, 1, 2;

and the pharmaceutically acceptable salts thereof; with the proviso that:

(a) when any of $R_1$, $R_5$ or $R_6$ is unsaturated loweralkyl, the unsaturation cannot be alpha to the nitrogen atom.

2. A compound of claim 1 wherein R is loweralkyl.

3. A compound of claim 1 wherein X and $X_1$ are both hydrogen.

4. A compound of claim 1 wherein $R_1$,$R_2$,$R_3$ and $R_4$ are hydrogen.

5. A compound of claim 1 wherein $R_5$ and $R_6$ are are $C_1$–$C_{12}$ straight or branched chain alkyl.

6. A compound of claim 1 wherein $R_1$ collectively with $R_5$ produces a piperazine ring.

7. A compound of claim 1 wherein R is loweralkyl, $R_5$ and $R_6$ are $C_1$–$C_{12}$ straight or branched chain alkyl and X,$X_1$,$R_1$,$R_2$,$R_3$ and $R_4$ are hydrogen.

8. A compound of claim 1 wherein R is loweralkyl, X, $X_1$, $R_2$, $R_3$, $R_4$, are hydrogen and $R_1$ with $R_5$ forms a piperazine ring.

9. A compound of claim 7 which is N-[2-(diethylamino)ethyl]-4-[(methylsulfonyl)amino]benzamide.

10. A compound of claim 7 which is N-[3-(diethylamino)propyl]-4-[(methylsulfonyl)amino]benzamide.

11. A compound of claim 7 which is 4-[(butylsulfonyl)amino-N-[2-(diethylamino)ethyl]benzamide.

12. A compound of claim 7 which is N-[2-(diethylamino)ethyl]-4-[(ethylsulfonyl)amino]benzamide.

13. A compound of claim 7 which is N-[4-(diethylamino)butyl]-4-[(methylsulfonyl)amino]benzamide.

14. A compound of claim 7 which is N-[2-(dimethylamino)ethyl]-4-[(methylsulfonyl)amino]benzamide.

15. A compound of claim 7 which is N-[2-(dipropylamino)ethyl]-4-[(methylsulfonyl)amino]benzamide.

16. A compound of claim 7 which is N-[2-(diisopropylamino)ethyl]-4-[(methylsulfonyl)amino]benzamide.

17. A compound of claim 1 which is (4-[(methylsulfonyl)amino]-N-[2-(4-morpholinyl)ethyl]benzamide.

18. A compound of claim 8 which is 4-methyl-1-[4-[(methylsulfonyl)amino]benzoyl]piperazine.

19. A compound of claim 1 which is 4-[(methylsulfonyl)amino]-N-[2-(1- piperidinyl)ethyl]benzamide.

20. A compound of claim 1 which is 4-[(methylsulfonyl)amino]-N-[2-(1-pyrrolidinyl)ethyl]benzamide.

21. A compound of claim 1 which is N-[2-(diethylamino)ethyl]-N-methyl-4-[(methylsulfonyl)amino]benzamide.

22. A compound of claim 1 which is 4-[(methylsulfonyl)amino]-N-[2-(2,2,6,6-tetramethylpiperidino)ethyl]benzamide.

23. A compound of claim 1 which is 4-[(methylsulfonyl)amino]-N-[2-(thiomorpholin-B 4-yl)ethyl]benzamide.

24. A compound of claim 1 which is 4-[(methylsulfonyl)amino]-N-[2-(1-oxothiomorpholin-4-yl)ethyl]benzamide.

25. A compound of claim 1 which is N-[4-[[2-(diethylamino)ethyl]aminocarbonyl]phenyl]benzenemethanesulfonamide.

26. A compound of claim 7 which is N-[2-(ethyl(heptyl)amino)ethyl-4-[(methylsulfonyl)amino]benzamide.

27. The method of treating arrhythmias in a mammalian subject in need thereof comprising administering to said subject an antiarrhythmically effective dose of a compound according to claim 1.

28. A pharmaceutical composition for treating arrhythmias comprising an antiarrhythmic effective amount of a compound of claim 1 together with a non-toxic pharmaceutically acceptable carrier.

* * * * *

UNITED STATES PATENT AND TRADEMARK OFFICE
CERTIFICATE OF CORRECTION

PATENT NO.  : 4,544,654

DATED       : October 1, 1985

INVENTOR(S) : David D. Davey, William C. Lumma, Jr., Ronald A. Wohl

It is certified that error appears in the above-identified patent and that said Letters Patent is hereby corrected as shown below:

Column 5, line 8 "about 31 50°C." should read ---about -50°C---.

Column 17, line 9 "(thiomorpholin-B 4-yl)" should read ---(thiomorpholin-4-yl)---.

Signed and Sealed this

Twelfth Day of August 1986

[SEAL]

Attest:

Attesting Officer

DONALD J. QUIGG

Commissioner of Patents and Trademarks